United States Patent [19]

Cleary et al.

[11] Patent Number: 4,847,073

[45] Date of Patent: Jul. 11, 1989

[54] ULTRAVIOLET RADIATION ABSORBING CYCLOHEXENYLIDENE METHOD

[75] Inventors: Thomas P. Cleary, Wilmington, Del.; Donald J. Gosciniak, West Chester, Pa.; Charalambos J. Phalangas, Wilmington, Del.

[73] Assignee: ICI Americas Inc., Wilmington, Del.

[21] Appl. No.: 212,824

[22] Filed: Jun. 29, 1988

[51] Int. Cl.$^4$ .................... A61K 7/40; A61K 7/42; A61K 7/44; A61K 9/10
[52] U.S. Cl. ............................ 424/59; 424/DIG. 1; 424/47; 424/63; 424/64; 514/938
[58] Field of Search .................. 558/401, 402; 424/59

[56] References Cited

U.S. PATENT DOCUMENTS

| 2,623,060 | 12/1952 | Cragoe et al. | 558/402 |
| 3,576,003 | 4/1971 | Strobel et al. | 424/59 |
| 4,008,681 | 5/1978 | Baumann et al. | 424/59 |
| 4,457,944 | 7/1984 | Conrad et al. | 424/59 |

OTHER PUBLICATIONS

Brooker et al., Chem. Abs., 1959, vol. 53, pp. 12899, 12900, 12901.
Kodak, Chem. Abs., 1960, vol. 54, pp. 2057, 2058.
Mukherji, Chem. Abs., 1965, vol. 59, p. 5031e.

*Primary Examiner*—Dale R. Ore

[57] ABSTRACT

Sunscreen compositions are described which contain certain cyclohexenylidenyl which act as UV filters when incorporated in a carrier in amounts ranging from 0.1–50% by weight.

6 Claims, No Drawings

ULTRAVIOLET RADIATION ABSORBING CYCLOHEXENYLIDENE METHOD

The present invention is directed to ultraviolet absorbing compositions comprising substituted cyclohexenylidenes and blends thereof which are useful as protective coatings and to a method for protecting substrates against the harmful effects of actinic radiation. It is further directed to a process for making ultraviolet absorbing coating compositions.

Ultraviolet radiation absorbing coatings are useful in protecting substrates such as plastic resins against accelerated deterioration and the skin of warm blooded animals against severe erythema, edema and blistering. The compositions of the invention are generally referred to as sunscreen compounds and blends thereof can be incorporated with waxes, oils, lacquers, soft resins in the preparation of furniture and auto polishes, cosmetics, suntan oils and lotions, lipsticks, hair treatments, skin formulations, contact lenses and the like.

In particular the invention relates to sunscreen compositions comprising a carrier having incorporated therein an effective amount of a filtering agent for ultraviolet radiation selected from a compound of Formula I:

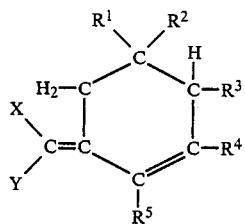

wherein:

X and Y are independently selected from the group —CN, —COOR$^6$, —CONHR$^6$, —CON(R$^6$)$_2$, —PhCOOR$^6$, —PhCOR$^6$, —PhN(R$^6$)$_2$, and wherein only one X or Y may be substituted with —H, and R$^1$, R$^2$, R$^3$, R$^4$ and R$^5$ are selected from the group of —H, —OH, —COOR$^6$, alkyl, alkoxy or hydroxyalkyl groups having 1-5 carbon atoms and R$^6$ is selected from H, alkyl, alkylaryl or arylalkyl groups of 1-22 carbon atoms.

Preferred compounds are those wherein X and Y are selected from —CN, —COOR$^6$, or —COR$^6$.

Most preferred compounds are those wherein at least one of the X and Y groups is —CN and the other is —COOR$^6$.

Of particular interest are compositions containing compounds of Formula I having substituent groups which provide selected absorption of actinic radiation in the 290-320 nm range as well as the 320-400 nm range of wavelength. The compounds may be present in the coating compositions as a finely divided solid or as a solute dispersed in an acceptable carrier when applied to a surface such that the selection of said carrier in the coating composition permits absorbancy in the 290-400 nm range.

The compositions of the invention comprise UV absorbing compounds of Formula I and others in amounts needed to provide protection against the harmful effects of ultraviolet radiation. The amount of concentration of these compounds in the composition is such that when the composition is topically applied, the desired protection is provided. The amount needed to provide the desired protection can vary with the characteristics of the compound i.e. its extinction coefficient or substantivity, the nature of the carrier, the source and intensity of the radiation and other well recognized variables. Suitable amounts can be readily determined by standard methods of testing. The UV filter compounds are incorporated in the carrier in an amount ranging from about 0.1% to about 50% by weight and usually in amounts of 0.5-30% by weight and preferably 1.0-15% by weight.

Carriers include any vehicle or medium capable of incorporating the UV filter compound in a manner permitting uniform topical application. For application on human skin, the carrier must be pharmaceutically acceptable. The term "pharmaceutically acceptable" is intended as a qualifier when the carrier is dermatologically innocuous to warm blooded animals and cosmetically acceptable, however all carriers are not useful on animal skin. The carrier may comprise a wax, oil or cream base material in which the agent can be held in a clear solution or a uniform dispersion, for example, as submicron size particles. Preferably the carrier comprises a suitable solvent or a mixture of solvents capable of dissolving the UV filter compounds to provide a concentration that is effective as a sunscreen agent when incorporated in the sunscreen formulation. Solvents which may be useful include alcohols, ketones, esters, polyolesters, such as oils, hydrocarbons, chlorinated hydrocarbons, ethers, polyethers, polyetherpolyols, and other special solvents such as dimethylsulfoxide, dimethylformamide, dimethylisosorbide, and the like. Such solvents are considered useful only if they do not permanently interact with the active filtering agents of the invention to shift the total effective absorption outside of the 290-400 nm range. Some of the above named ingredients are not pharmaceutically acceptable, but are useful in other applications.

The sunscreening compositions may be applied as a clear liquid or as a lotion comprising a water-in-oil, an oil-in-water or a multiple emulsion. Either the oil or water base or both may be used as a carrier for the sunscreening compositions of the invention. The oil base material and the water and oil base compositions will form a continuous film of the UV filtering compound. Such films also provide protection against sun induced erythema. Sunscreening formulations are generally used in hot weather and at beaches were people enjoy bathing activities. It is therefore desirable that the protective coating applied to the skin is not appreciably affected by water or perspiration. The compositions herein disclosed are included in a thin layer protective coating on a skin of warm blooded animals and provide long lasting protection against erythema and do not appreciably decompose over practical periods of exposure to sunlight.

The cyclohexenylidenes are conveniently made by condensing acetate or malonate derivatives with an appropriate ketone in the presence of catalyst. The cyclohexenyl ketones can be synthesized by condensing 3-oxoesters with aqueous formaldehyde/dialkylamines in presence of acid catalyst. Procedures are available in the literature such as Org. Mag. Res., 15 339 (1981) and J. Chem. Soc. 1570 (1926). Representative compounds useful in the practice of the invention are listed in Table 1 which are made according to the following procedures:

(I) Representative Procedure for Cyanoacetate/Ketone Condensation:

[Preparations 1,2,3,7,10,11,12,13,17,18,20,21 and 22]

A mixture of isophorone (2,484 g, 18 mol), methyl cyanoacetate (1,782 g, 18 mol), acetic acid (1,080ml, 18 mol) and ammonium acetate (280 g 3.6 mol) in cyclohexane (1,500 ml) was heated at reflux for 3 hrs. with continuous removal of water through a Dean Stark trap. The reaction was cooled to room temperature and washed with water (1×500 ml), sat. $NaHCO_3$ (1×500 ml) and brine (1×500 ml). The organic layer was separated, dried over anhydrous $Na_2SO_4$, filtered and concentrated. Distillation of the crude reaction mixture at reduced pressure yields methyl-2-(3,5,5-trimethyl-2-cyclohexenylidene) cyanoacetate (75%). Ref: Org. Mag. Res., 1981, 15, 339 and references therein.

(II) Representative Procedure for Amides and Amide Dimers:

[Preparation 23]

A mixture of methyl 2(3,5,5-trimethyl-2-cyclohexenylidene) cyanoacetate (0.2 mol), aniline (0.2 mol), sodium methoxide powder (0.22 mol) and dry benzene (200 mls) was refluxed for 7 hours, cooled, and poured carefully into 10% HCl (200 mls). This mixture was cooled and stirred in an ice bath while hexane (200 mls) was added. The resulting slurry was filtered, washed with water (100 mls) and hexane (50 mls), and air dried yielding N-phenyl 2(3,5,5-trimethyl-2-cyclohexenylidene) cyanoacetamide. Ref: J. Org. Chem., 1963, 28, 2915 and references therein.

(III) Representative Procedure for Esters and Ester Dimers:

[Preparations 4-6]

A mixture of methyl 2(3,5,5-trimethyl-2-cyclohexenylidene) cyanoacetate (4.54 mmol), isopropanol (45.6 mmol) and $LiNH_2$ (0.2 g) was heated under a strong nitrogen flow in a distillation apparatus. After 3 hrs the reaction was cooled to room temperature and neutralized with acetic acid. Ethyl acetate (50 mls) was added and the organic phase separated, washed with water (2×20 ml), sat. $NaHCO_3$ (1×20 ml) and brine (1×10 ml), dried over $MgSO_4$, filtered and concentrated. Isopropyl 2(3,5,5-trimethyl-2-cyclohexenylidene) cyanoacetate was isolated by flash distillation. Ref: U.S. Pat. No. 3,511,812.

(IV) Representative Procedure for Hydroxyesters or Hydroxyamides:

[Preparation 8]

A mixture of methyl 2(3,5,5-trimethyl-2-cyclohexenylidene) cyanoacetate (0.4 mol), 2,2-dimethyl-1,3-propanediol (1.8 mol), $LiNH_2$ (0.5 g) and cyclohexane (400 mls) was refluxed under a Dean-Stark trap for 20 min. The reaction was cooled to room temperature and neutralized with acetic acid. Ethyl acetate was added, the organic phase washed with water, sat. $NaHCO_3$, and brine, dried over $MgSO_4$, filtered and 2,2-dimethyl-3-hydroxypropyl 2(3,5,5-trimethyl-2-cyclohexenylidene) cyanoacetate isolated. Ref: U.S. Pat. No. 4,263,222.

(V) Representative Procedure for Amides, Esters, Amide Dimers, Ester Dimers, and Mixed Amide-Ester Dimers:

[Preparations 1-6, 8 and 9]

2(3,5,5-trimethyl-2-cyclohexenylidene) cyanoacetic acid (0.2 mol) and thionyl chloride (50 mls) were refluxed together for 1 hr. The acid chloride was then added dropwise with stirring to n-butylamine (0.4 mol) in petroleum ether (340 mls). The flask may have to be cooled with an ice bath. After addition, 1N HCl (150 mls) was added and the mixture stirred. The mixture was allowed to separate and the upper layer was washed until acid free. It was then treated with 1.4 g activated carbon, then n-butyl (3,5,5-trimethyl-2-cyclohexenylidene) cyanoacetamide was isolated. Ref. J. Am. Chem. Soc., 1949, 71, 2215.

(VI) Representative Procedure for Synthesis of 3-Methyl-4,6-dicarboalkoxy-2-cyclohexen-1-one:

Piperidine (20 ml) was added to a mixture of ethylacetoacetate (520 g, 4 mol) ad paraformaldehyde (60 g, 2 mol). The mixture soon became very hot and it was necessary to plunge the flash into an ice-bath occasionally in order to control the reaction. After the vigorous reaction subsided the mixture was heated on the steam bath for 40 min. The yellow viscous oil (3-methyl-4,6-dicarboethoxy-2-cyclohexen-1-one) was separated from the supernatent water and dried over $Na_2SO_4$. Ref: J. Am. Chem. Soc., 1943, 65, 631.

This compound condenses with ethyl cyanoacetate as in example 14 (process related to procedure I) to provide preparation 10.

(VII) Representative Procedure for 4- Substituted Cyclohexenones:

To a mixture of methylmagnesium bromide in ether (400 ml, 0.8 mol) and $FeCl_3$ (2.0 g), a solution of isophorone (83 g, 0.6 mol) in ether (100 ml) was added dropwise at −20° C., and the mixture stirred for 0.5 hr. TMSCl (87 g, 0.8 mol), triethylamine (60 ml), and HMPT (60 ml) were successively added at 0° C. and the mixture stirred at room temperature for 24 hrs. The mixture was poured into cold water and extracted with hexane. The extract was washed with sat'd $KHSO_4$, sat'd $NaHCO_3$, and brine, then dried over $MgSO_4$. The solvent was stripped and the residue distilled.

To a −60° C. solution of the above silyl enol-ether (20 mmol) and crotonaldehyde (24 mmol) in $CH_2Cl_2$ (20 ml) was added a solution of $TiCl_4$ (20 mmol) in $CH_2Cl_2$ (5 ml). After stirring for 2 hrs., the mixture was quenched with water. The $CH_2Cl_2$ layer was stirred further with a 10% solution of adipic acid for 24 hrs. at room temperature and washed with sat'd $NaHCO_3$ and brine, then dried over $MgSO_4$. The solvent was stripped and the residue chromatographed to yield 3,5,5-trimethyl-4-hydroxybutenyl-2-cyclohexen-1-one. Ref: Bull. Chem. Soc. Jpn., 1982, 55, 1907.

This condenses with ethyl cyanoacetate under the conditions of procedure I to provide compound 24.

(VIII) Representative Procedure for Malonate/Ketone Condensation:

[Preparation 19]

A mixture of $TiCl_4$ (5 ml) in $CCl_4$ (5 ml) was added dropwise to THF (20 ml) at 0° C. and under $N_2$. Isophorone (2.9 g, 21 mmol) and dimethyl malonate (3.2 g, 24 mmol) in THF (5 ml) was added dropwise, then pyridine (7.5 ml) in THF (4 ml) was added dropwise. The mixture was stirred at 0° C. for 30 min., then at RT for 1 hr.

The reaction was quenched with water, diluted with ether, the organic phase washed with sat'd $NaHCO_3$, dried, and the volatiles stripped under vacuum, then distilled to yield the diester.

The following examples serve as nonlimiting illustrations of the types of compounds included in the invention and all parts of percentages are expressed on a weight basis unless otherwise specified.

TABLE 1

| Prep. No. | $R^1$ | $R^2$ | $R^3$ | $R^4$ | $R^5$ | X | Y | λMAX | K |
|---|---|---|---|---|---|---|---|---|---|
| 1 | $CH_3$ | $CH_3$ | H | $CH_3$ | H | CN | $COOCH_3$ | 305 | 113 |
| 2 | H | H | H | $CH_3$ | H | CN | $COOCH_3$ | 305 | 120 |
| 3 | $C_3H_5$ | H | H | H | $CH_3$ | CN | $COOCH_3$ | 294 | 74 |
| 4 | $CH_3$ | $CH_3$ | H | $CH_3$ | H | CN | $COOC_5H_{11}$ | 304 | 86 |
| 5 | $CH_3$ | $CH_3$ | H | $CH_3$ | H | CN | $COOC_4H_9$ | 304 | 94 |
| 6 | $CH_3$ | $CH_3$ | H | $CH_3$ | H | CN | $COOC_3H_7$ | 304 | 96 |
| 7 | $CH_3$ | $CH_3$ | H | $CH_3$ | H | CN | $C_6H_5$ | 259,317 | 55.65 |
| 8 | $CH_3$ | $CH_3$ | H | $CH_3$ | H | CN | $COOC_5H_{11}O$ | ca.304 | ca.77 |
| 9 | $CH_3$ | $CH_3$ | H | $CH_3$ | H | CN | $COOC_{10}H_{21}$ | ca.304 | ca.62 |
| 10 | H | H | $COOC_2H_5$ | $CH_3$ | H | CN | $COOC_2H_5$ | 300 | 101 |
| 11 | $CH_3$ | $CH_3$ | H | $CH_3$ | H | CN | COOH | 302.5 | 105 |
| 12 | $CH_3$ | H | H | $CH_3$ | H | CN | COOH | ca.304 | ca.118 |
| 13 | $CH_3$ | H | H | $CH_3$ | H | CN | $COOC_2H_5$ | ca.304 | ca.103 |
| 14 | $CH_3$ | $CH_3$ | H | $CH_3$ | H | CN | $COOC_2H_5$ | ca.304 | ca.97 |
| 15 | H | H | H | * | H | CN | $COOC_2H_5$ | — | — |
| 16 | $CH_3$ | $CH_3$ | H | * | H | CN | $COOC_2H_5$ | — | — |
| 17 | H | H | H | $CH_3$ | H | CN | COOH | ca.304 | ca.127 |
| 18 | H | H | H | $CH_3$ | H | CN | $COOC_2H_5$ | ca.304 | ca.110 |
| 19 | $CH_3$ | $CH_3$ | H | $CH_3$ | H | $COOCH_3$ | $COOCH_3$ | 284 | 81 |
| 20 | $CH_3$ | $CH_3$ | H | $CH_3$ | H | CN | CN | 302 | 129 |
| 21 | H | H | $COOC_2H_5$ | $CH_3$ | H | CN | CN | 300 | 122 |
| 22 | $CH_3$ | $CH_3$ | H | $CH_3$ | H | H | COOH | 274 | 125 |
| 23 | $CH_3$ | $CH_3$ | H | $CH_3$ | H | CN | CONHPh | ca.304 | ca.70 |
| 24 | $CH_3$ | $CH_3$ | $C_4H_7$ | $CH_3$ | H | CN | $COOC_2H_5$ | ca.304 | ca.77 |

Ref.: Ukr. Khim. Zh. (Russ. Ed.), 1975, 41, 284
*(3-ethyl-2(3H)—benzothiazolylidene)methyl It has been established that the actinic radiation between 290 nm and 320 nm produces a susbstantial portion of the burning or erythema and tanning energy while the radiation between 320 nm and 400 nm is less erythemogenic but more tanning. The cosmetic industry has divided these spectra into the burning range UV-B (290–320 nm) and the tanning range UV-A (320–400 nm). Since approximately 76% of the physiological tanning potential of sunlight is found in the UV-B range and the balance is found in the UV-A range, it is desirable to have a substantial amount of the radiation in those ranges filtered out before it produces a harmful effect on the surface of human skin. While sunscreen lotions have been formulated to be most effective in the UV-B range more recent studies have indicated that it is desirable to have collective adsorption in the UV-A range as well. It has been difficult to find a practical compound which effectively adsorbs in both ranges. Therefore, formulators must resort to the combination of two or more compounds which are each effective either in the UV-B or UV-A range to provide maximum skin protection. Usually no one compound falling within the definition of Formula I is effective over the entire 290–400 nm range and therefore either two or more compounds of Formula I can be selected and blended within the formulation of varying concentrations until the desired balance between burning and tanning is accomodated. Compounds of Formula I can be blended with sunscreening compounds from other chemical families to obtain the desired balance of protection between 290–400 nm region of the UV spectrum. Such a combination is shown in Example 21. It is preferred to have a formulation having at least one compound which absorbs in the 320–400 nm range. At least one can be selected from Formula I.

The use of the UV filters of the invention can be demonstrated in lotion formulations which are topically applied to the surface of the skin. The effectiveness of the UV light absorbers are tested on human subjects by treating a 1 cm square section of a subjects' back with predetermined amounts of sunscreen lotion, exposing the treated areas to UV light for a set period of time and thereafter making a visual comparison with untreated and fully masked skin areas. The SPF (skin protection factor) is calculated by comparing the effects of radiation on protected skin with the unprotected skin.

Besides the SPF determinations on humans, many in vitro methods and in vivo tests on animal models are also widely used. Some of these methods yield results which correlate well with SPF determined on humans and are useful tools for evaluating new compounds.

The following lotions and creams will serve to illustrate but not limit those which can be used in the practice of the invention.

In general, typical formulating techniques are well known to skilled formulators and usually require that the filtering agent be first added to the oil phase which is thereafter emulsified. With regards to examples 1–10 and controls all ingredients can be mixed together and stirred in conventional apparatus. Since in many cases a single compound used at a reasonable concentration does not effectively protect throughout the whole region of the earth reaching solar UV radiation, blends of two or more UV absorbers can be used in a formulation to afford greater protection. To illustrate the effectiveness of the compounds of the invention in sunscreen formulations, compounds of Preparations 1 and 2 were formulated into creams and lotions for testing. The formulations of Examples 1–10 are shown in Table 2.

Examples 1-10

Blending Procedure for Examples 1, 2, 5-8:

Heat mixed ingredients of (A) to 70° C. Heat mixture B to 75° C. then add to (A). Add (C).

Examples 3, 4, 9 and 10 are clear solutions of (E).

TABLE 2

Sunscreen Formulations

| Ingredient | 1 | 2 | 3 | 4 | 5 | 6 | 7 | 8 | 9 | 10 |
|---|---|---|---|---|---|---|---|---|---|---|
| Preparation No. 1 | 8 | 3 | 8 | 3 | — | — | — | — | — | — |
| Preparation No. 2 | — | — | — | — | 8 | 8 | 3 | 8 | 8 | 3 |
| Mineral Oil | 5 | 5 | — | — | 5 | 5 | 5 | 5 | — | 0 |
| Stearyl Alcohol | .5 | .5 | — | — | .5 | .5 | .5 | .5 | 0 | — |
| 21 Dendro Steorylether (Brij 721 ICI Americas) | 2.5 | 2.5 | — | — | 2 | 1.5 | 1.5 | 2.6 | — | — |
| 21 Dendro Steorylether (Brij 721 ICI Americas) | 1.5 | 1.5 | — | — | 2 | 2.5 | 2.5 | 1.4 | — | — |
| Silicone Oil SF96 (G.E.) | .5 | .5 | — | — | .5 | .5 | .5 | .5 | — | — |
| Cetyl Alcohol | .5 | .5 | — | — | — | .5 | .5 | — | — | — |
| (B) | | | | | | | | | | |
| Water | 70.95 | 75.95 | — | — | 71.45 | 70.95 | 75.95 | 71.45 | — | — |
| Carbopol 934 2% sln. | 10 | 10 | — | — | 10 | 10 | 10 | 10 | — | — |
| (C) | | | | | | | | | | |
| Sodium Hydroxide (10% aqueous) | .2 | .2 | — | — | .2 | .2 | .2 | .2 | — | — |
| (D) | | | | | | | | | | |
| DMDMH-55 (Glyco) | .35 | .35 | — | — | .35 | .35 | .35 | .35 | — | — |
| (E) | | | | | | | | | | |
| Dimethylisosorbide (Atlas G100) | — | — | 92 | 97 | — | — | — | — | 92 | 97 |
| Physical Form | | | | | | | | | | |
| Emulsion | X | X | | | X | X | X | X | | |
| Solution | | | X | X | | | | | X | X |

The formulation of Examples 3 and 9 were each applied to 8 specimens of excised hairless mouse epidermis at a level of 1 mg/cm$^2$. The epidermis was exposed to UV radiation in the UV-B and UV-A range and compared with unprotected skin similarly exposed. Average Test results for SPF are listed in Table 3.

TABLE 3

| Example | Peak Absorption (nm) | Mol Extinct Co-efficient Mol. Wt. | SPF UV-B | SPF UV-A | Standard Deviation UV-B | Standard Deviation UV-A |
|---|---|---|---|---|---|---|
| 3 | 305 | 102.6 | 7.32 | 1.32 | 2.89 | 0.145 |
| 9 | 304 | 119 | 14.0 | 1.73 | 2.2 | 0.164 |
| Control 100% (E) | — | — | 01.0 | 01.0 | 0 | 0 |

TABLE 4

Sunscreen Formula

| Ingredient | 11 | 12 | Control D |
|---|---|---|---|
| Preparation No. 2 | 2 | 8 | 0 |
| Petrolatum (Snow White USP) | 35 | 35 | 35 |
| Polyoxyethylene (21) stearyl ether | 1.16 | 1.16 | |
| Polyoxyethylene (2) stearyl ether | 3.86 | 3.86 | 3.86 |
| Silicone Oil | 3 | 3 | 3 |
| Water (deionized) | 54.08 | 48.08 | 56.08 |
| Carbopol ® 934 | 0.4 | 0.4 | 0.4 |
| Sodium Hydroxide (10%) | 0.4 | 0.4 | 0.4 |
| Dowicil ® 200 | 0.1 | 0.1 | 0.1 |
| Physical Form | cream | cream | cream |

Additional tests on female subjects ranging from ages 27-50 having skin type I (always burns easily, never tans), type II (always burns easily, tans minimally) and type III (burns moderately, tans gradually) were performed and each subject was exposed to UV radiation on 3 separate days at 27, 28 and 29 (mW/cm$^2$) respectively. Templates are applied to individual skin sites on designated areas of the back. Application of the test material are made by uniformly spreading the lotion or cream over a 50 cm$^2$ area (3.5 cm by 14.3 cm) at a dose of 2mg/cm$^2$ with a finger cot. Approximately 15 minutes after application the sites were irradiated. Test sites are scored approximately 24 hours after exposure.

In addition to their use in coating skin to prevent sunburn the compositions of the invention can also be employed in various formulations such as waxes, oils, lacquers and soft resins in the preparation of furniture and auto polishes, cosmetics, lipstick, hair treatments, skin formulations and contact lenses. The compounds of the invention act as filtering agents and may be used singly or in combination to provide a wider range of protection. The following formulations are given to demonstrate a few of the many applications.

| Example No. | Filtering Agent | Carrier Ingredients | Composition (% by Wt) |
|---|---|---|---|
| 13 | Aerosol Hairdressing | | |
| | Prep 2 | | 5.0 |
| | | Decaglycerol monolaurate | 2.0 |
| | | Polypropylene (200) monooleate | 3.0 |
| | | Ethoxylated (10) lanolin alcohols | 1.0 |
| | | Propylene glycol | 2.0 |
| | | Ethyl alcohol, anhydrous | 39.5 |
| | | Protein polypeptide (20% alcoholic) | 1.2 |
| | | Isopropyl myristate | 1.3 |
| | | Propellant 11 | 15.0 |
| | | Propellant 12 | 30.0 |
| | | Water | q.s. |

Procedure for Formula: Dissolve all ingredients in slightly warmed ethylalcohol, avoiding loss of the alcohol, add the water, and agitate well to disperse any haze. Filter the concentrate and fill into aerosol containers. Add propellants.

| | | | |
|---|---|---|---|
| 14 | Formula for Creamy Type Lipstick Base | | |
| | Prep 1 | | 5 |
| | | Carnauba wax | 3 |
| | | Candelilla wax | 7 |
| | | Ozokerite ® | 3 |

| Example No. | Filtering Agent | Carrier Ingredients | Composition (% by Wt) |
|---|---|---|---|
| | | Beeswax | 7 |
| | | Lanolin | 10 |
| | | Castor oil | 60 |
| | | Isopropyl myristate | 5 |
| | | Perfume | q.s. |
| 15 | Water-In-Oil (W/O), Detergent Resistant, Liquid Auto Polish | | |
| | Part A | 2.00% Durmont ® 500 Montan Wax | (Dura Commodities) |
| | Part B | 0.75% DC 530 Silicone Fluid | (Dow Corning) |
| | | 4.25% DC 531 Silicone Fluid | |
| | | 1.50% SPAN ® 80 | |
| | | 10.00% Kerosene | |
| | | 16.50% Stoddard Solvent | |
| | | 5.0% Preparation 1 | |
| | Part C | 10.00% Kaopolite ® SFO | (Kaopolite) |
| | Part D | 50.00% Water | |
| | Method of Preparation: | | |
| | 1. Melt wax in Part A (85–90° C.) | | |
| | 2. Add Part B ingredients to melted wax and stir to blend well. Return temperature to 85–90° C. | | |
| | 3. Add Part C to Part A/Part B blend and mix until uniform with medium agitation. Keep temperature in the 85–90° C. range. | | |
| | 4. Heat Part D to 95° C. and slowly add to the blend with high speed stirring until emulsion is obtained. | | |
| | 5. Cool to 40–45° C. with continuous stirring. | | |
| | 6. Homogenize. | | |
| 16 | Neutral Base Lacquer | | |

| Materials | Pounds |
|---|---|
| Urethane 60% N.V. | 32 |
| Long oil alkyd 60% N.V. | 352 |
| Triton X-45 | 7.5 |
| Nuxtra ® Calcium 6% | 12 |
| Bentone Jell 8% | 28 |
| Disperse the bentone jell under high speed cowles and add: | |
| Preparation 1 | 16 |
| Low odor mineral spirits | 85 |
| Cyclodex ® cobalt 6% | 3 |
| JK 270-70% | 76 |
| Water | 205 |
| Anti skin | 2 |
| Viscosity: | 80–85 KU |
| W/G: | 7.84 |
| 60° Gloss: | 85 |
| SAG: | 6 ml |

| Example No. | Filtering Agent | Carrier Ingredients | Composition (% by Wt) |
|---|---|---|---|
| 17 | O/W Paraffin Wax Emulsion | | |
| | Part A | 50% Paraffin Wax | |
| | | 5% SPAN ® 60/TWEEN ® 60 (50/50) | |
| | | 5% Preparation 2 | |
| | Part B | 40% Water | |
| | Method of Preparation: | | |
| | 1. Melt Part A ingredients together and heat to 80° C. | | |
| | 2. Heat Part B to 85° C. | | |
| | 3. Add Part B to Part A slowly with moderate agitation until inversion occurs. Add remaining water rapidly. | | |
| | 4. Cool in cold water bath with slow agitation to approximately 35° C. | | |
| 18 | O/W Soft Microcrystalline Wax Emulsion | | |
| | Part A | 30% Microcrystalline wax (Ultraflex Amber Wax-Petrolite Corp.) | |
| | | 30% SPAN 60/TWEEN 60 (78/22) | |
| | | 5% Preparation 1 | |
| | Part B | 62% Water | |
| | Method of Preparation: | | |
| | 1. Melt together Part A ingredients and heat to 80–90° C. | | |
| | 2. Heat Part B to boiling. | | |
| | 3. Add Part B to Part A slowly with moderate agitation until inversion occurs. Add remaining water rapidly. | | |
| | 4. Remove from heat and cool to room temperature without stirring. | | |
| 19 | O/W Carnauba Wax Emulsion | | |
| | Part A | 10% Carnauba wax | |
| | | 3% TWEEN 80 (ICI Americas) | |
| | | 5% Preparation 2 | |
| | Part B | 82% Water | |
| | Method of Preparation: | | |
| | 1. Melt Part A ingredients together and heat to 95° C. and hold. | | |
| | 2. Heat Part B to boiling. | | |
| | 3. Add Part B to Part A slowly with moderately fast stirring until inversion occurs. Add remaining water rapidly. | | |
| | 4. Remove emulsion from heat and cool rapidly with stirring. | | |

SUNSCREEN LOTION

EXAMPLE 20

| PHASE | INGREDIENTS (SUPPLIERS) | PERCENT BY WEIGHT |
|---|---|---|
| A | Petrolatum, Snow White USP (Ruger) | 35.00 |
| | Brij ® 721 (ICI Americas) | 1.16 |
| | Brij ® 72 (ICI Americas) | 3.86 |
| | Silicone Oil, 350 cs (Ruger) | 3.00 |
| | Preparation 2 | 5.00 |
| | Uvinul M-40 (BASF) | 3.00 |
| B | Water | 48.08 |
| | Carbopol ® 934 (B. F. Goodrich) | 0.40 |
| C | Sodium Hydroxide (10% Aqueous Solution) | 0.40 |
| D | Dowicil ® 200 (DOW Chemical) | 0.10 |

Preparation: Heat (A) to 60° C. Heat (B) to 65° C. Add (B) to (A) slowly with moderate agitation. Add (C). Cool to 50° C. Add (D). Cool, while stirring to 35° C.

SUNSCREEN LOTION

EXAMPLE 21

| PHASE | INGREDIENTS (SUPPLIERS) | PERCENT BY WEIGHT |
|---|---|---|
| A | Arlamol ® E (ICI Americas) | 7.00 |
| | Stearyl Alcohol | 2.50 |
| | Silicone Oil, 350 cs (Ruger) | 5.00 |
| | Arlasolve ® 200 (ICI Americas) | 2.10 |
| | Brij ® 72 (ICI Americas) | 4.90 |
| | Preparation 2 (UVB absorber) | 5.00 |
| | Dimethyl Ester Nophtholenzlidene Malonate (UVA absorber) | 3.00 |
| B | Water | 70.00 |
| | Carbopol 934 (B. F. Goodrich) | 0.20 |
| C | Sodium Hydroxide (10% Aqueous Solution) | 0.20 |
| D | Dowicil 200 (DOW) | 0.10 |

Preparation: Heat (A) to 65° C. Heat (B) to 70° C. Add (B) to (A) slowly with moderate agitation. Add (C). Cool to 50° C. Add (D). Cool, while stirring to 35° C.

SUNSCREEN LOTION

EXAMPLE 22

| PHASE | INGREDIENTS (SUPPLIERS) | PERCENT BY WEIGHT |
|---|---|---|
| A | Arlamol E (ICI) | 7.00 |
|  | Stearyl Alcohol | 2.50 |
|  | Silicone Oil, 350 cs (Rugher) | 5.00 |
|  | Arlasolve 200 (ICI) | 2.10 |
|  | Brij 72 (ICI) | 4.90 |
|  | Preparation 2 | 8.00 |
| B | Water | 70.00 |
|  | Carbopol 934 (B. F. Goodrich) | 0.20 |
| C | Sodium Hydroxide (10% Aqueous Solution) | 0.20 |
| D | Dowicil 200 (DOW) | 0.10 |
| Preparation: Heat (A) to 60° C. Heat (B) to 65° C. Add (B) to (A) slowly with moderate agitation. Add (C). Cool to 50° C. Add (D). | | |

SUNSCREEN LOTION

EXAMPLE 23

| PHASE | INGREDIENTS (SUPPLIERS) | PERCENT BY WEIGHT |
|---|---|---|
| A | Petrolatum, Snow White USP (Ruger) | 35.00 |
|  | Brij 721 (ICI) | 1.16 |
|  | Brij 72 (ICI) | 3.86 |
|  | Preparation 1 | 8.00 |
|  | Silicone Oil, 350 cs (Ruger) | 3.00 |
| B | Water | 49.08 |
|  | Carbopol 934 (B. F. Goodrich) | 0.40 |
| C | Sodium Hydroxide (10% Aqueous Solution) | 0.40 |
| D | Dowicil 200 (DOW) | 0.10 |
| Preparation: Heat (A) to 60° C. Heat (B) to 65° C. Add (B) to (A) slowly with moderate agitation. Add (C). Cool to 50° C. Add (D). Cool, while stirring to 35° C. | | |

SUNSCREEN LOTION

EXAMPLE 24

| PHASE | INGREDIENTS (SUPPLIERS) | PERCENT BY WEIGHT |
|---|---|---|
| A | Arlamol E (ICI) | 7.00 |
|  | Stearyl Alcohol | 2.50 |
|  | Silicone Oil, 350 cs (Ruger) | 5.00 |
|  | Arlasolve 200 (ICI) | 2.10 |
|  | Brij 72 (ICI) | 4.90 |
|  | Preparation 2 | 5.50 |

| PHASE | INGREDIENTS (SUPPLIERS) | PERCENT BY WEIGHT |
|---|---|---|
| B | Water | 72.50 |
|  | Carbopol 934 (B. F. Goodrich) | 0.20 |
| C | Sodium Hydroxide (10% Aqueous Solution) | 0.20 |
| D | Dowicil 200 (DOW) | 0.10 |
| Preparation: Heat (A) to 65° C. Heat (B) to 70° C. Add (B) to (A) slowly with moderate agitation. Add (C). Cool to 50° C. Add (D). Cool, while stirring to 35° C. | | |

What is claimed is:

1. A method for protecting a substrate against the effects of ultraviolet radiation by topically applying a composition comprising a carrier having incorporated therein an effective amount of a compound having Formula I

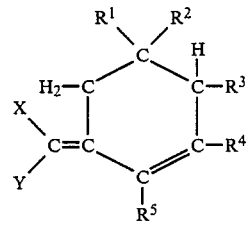

wherein:

X and Y are independently selected from the group consisting of $-CN$, $-COOR^6$, $-CONHR^6$, $-CON(R^6)_2$, $-PhCOOR^6$, $-PhCOR^6$, and $-PhN(R^6)_2$, and wherein only one X or Y may be substituted with $-H$, and $R^1$, $R^2$, $R^3$, $R^4$ and $R^5$ are selected from the group consisting of $-H$, $-OH$, $-COOR^6$, alkyl, alkoxy and hydroxyalkyl groups having 1–5 carbon atoms and $R^6$ is selected from the group consisting of H, alkyl, alkylaryl and arylalkyl groups of 1–22 carbon atoms.

2. A method of claim 1 wherein X and Y are selected from the group consisting of $-CN$, $-COOR^6$, and $-COR^6$ and are incorporated in said method in an amount ranging from about 0.1 to about 50% by weight.

3. A method of claim 2 wherein at least one of the X and Y groups is $-CN$ and the other is $-COOR^6$ incorporated in said method in an amount ranging from about 1 to about 15% by weight.

4. A method of claim 1 wherein said compound is dissolved in said carrier.

5. A method of claim 1 wherein said carrier is an aqueous emulsion.

6. A method of claim 1 wherein said substrate is the skin of a warm blooded animal.

* * * * *

UNITED STATES PATENT AND TRADEMARK OFFICE
CERTIFICATE OF CORRECTION

PATENT NO. : 4,847,073

DATED : July 11, 1989

INVENTOR(S) : Thomas P. Cleary et al

It is certified that error appears in the above-identified patent and that said Letters Patent is hereby corrected as shown below:

In The Specification:

Column 1, line 39, "-CN, $-COOR^6$, $-CONHR^6$, $-CON(R^6)_2$, -Ph-" should read ---CN, $-COR^6$, $-COOR^6$, $-CONHR^6$, $-CON(R^6)_2$, -Ph-".

Column 2, line 48, "were" should read --where--.

Column 4, line 23, "(520g, 4 mol) ad" should read --(520g, 4 mol) and--.

In The Examples:

Column 7, line 55 "Polyoxyethylene (21) stearyl ether   1.16   1.16" should read --Polyoxyethylene (21) stearyl ether   1.16   1.16   1.16--.

In The Claims:

Column 12, line 32 "consisting of -CN, $COOR^6$, $-CONHR^6$," should read --consisting of -CN, $COR^6$, $COOR^6$, $-CONHR^6$,--.

Signed and Sealed this

Ninth Day of October, 1990

Attest:

HARRY F. MANBECK, JR.

Attesting Officer    Commissioner of Patents and Trademarks